(12) United States Patent
Peng

(10) Patent No.: US 11,412,932 B1
(45) Date of Patent: Aug. 16, 2022

(54) SYSTEMS AND METHODS OF MULTI-IMPLANT PATTERNED BRAIN IMAGING AND STIMULATION

(71) Applicant: PhotonEdge Inc., Pleasanton, CA (US)

(72) Inventor: Song Peng, Pleasanton, CA (US)

(73) Assignee: PHOTONEDGE, INC., Pleasanton, CA (US)

( * ) Notice: Subject to any disclaimer, the term of this patent is extended or adjusted under 35 U.S.C. 154(b) by 546 days.

(21) Appl. No.: 16/194,383

(22) Filed: Nov. 18, 2018

Related U.S. Application Data

(60) Provisional application No. 62/588,898, filed on Nov. 20, 2017, provisional application No. 62/588,088, filed on Nov. 17, 2017.

(51) Int. Cl.
  *A61B 5/00*  (2006.01)
  *A61B 1/06*  (2006.01)
  *A61B 1/04*  (2006.01)
  *A61N 1/05*  (2006.01)

(52) U.S. Cl.
  CPC .......... *A61B 5/0042* (2013.01); *A61B 1/0669* (2013.01); *A61B 5/4064* (2013.01); *A61N 1/0529* (2013.01); *A61B 1/042* (2013.01)

(58) Field of Classification Search
  CPC ... A61B 5/0042; A61B 1/0669; A61B 5/4064; A61B 1/042; A61B 1/0661; A61B 1/07; A61N 1/0529; A61M 2039/0279
  See application file for complete search history.

(56) References Cited

U.S. PATENT DOCUMENTS

| 10,039,934 B2 | 8/2018 | Peng | |
| 2009/0054791 A1* | 2/2009 | Flusberg | A61B 5/0059 600/478 |
| 2009/0105726 A1* | 4/2009 | Sugiyama | A61B 1/0051 606/130 |
| 2009/0142017 A1* | 6/2009 | Merlet | G02B 27/642 385/26 |
| 2017/0258528 A1* | 9/2017 | Bai | G02B 23/2415 |

FOREIGN PATENT DOCUMENTS

WO  WO-2017174998 A1 * 10/2017 ......... A61B 1/00009

OTHER PUBLICATIONS

Zong et al. Fast high-resolution miniature two-photon microscopy for brain imaging in freely behaving mice. Nat Methods. Jul. 2017; 14(7)713-719. doi: 10.1038/nmeth.4305. Epub May 29, 2017. PMID: 28553965. (Year: 2017).*

(Continued)

*Primary Examiner* — Amanda Lauritzen Moher
*Assistant Examiner* — Delia M. Appiah Mensah
(74) *Attorney, Agent, or Firm* — Radlo & Su; Peter Su

(57) ABSTRACT

The present disclosure is directed to instruments and methods that provide one or more stimulations with multiple fibers and multiple imaging implants inserted in a subject for capturing images from one or more regions of the subject's brain. The microendoscope can include a single spatial light modulator or multiple spatial light modulators, a furcated imaging fiber bundle with multiple fibers, multi-implants coupled to a subject for multi-implant patterned brain imaging and stimulation. Both the single spatial light modulator and multiple spatial light modulators are capable to project optical patterns to different imaging fibers and thereby stimulate multiple regions of the brain.

18 Claims, 8 Drawing Sheets

(56) References Cited

OTHER PUBLICATIONS

Lane PM, Dlugan AL, Richards-Kortum R, Macaulay CE. Fiber-optic confocal microscopy using a spatial light modulator. Opt Lett. Dec. 15, 2000;25(24):1780-2. doi: 10.1364/ol.25.001780. PMID: 18066342. (Year: 2000).*

Photometrics: "Introduction to Splitters"; [Online: https://www.photometrics.com/products/imaging-splitters/introduction-to-splitters] (Year: 2021).*

Zong et al. Fast high-resolution miniature two-photon microscopy for brain imaging in freely behaving mice: Supplemental Figure 3a. Nat Methods. Jul. 2017;14(7):713-719. doi: 10.1038/nmeth.4305. Epub May 29, 2017. PMID: 28553965.*

* cited by examiner

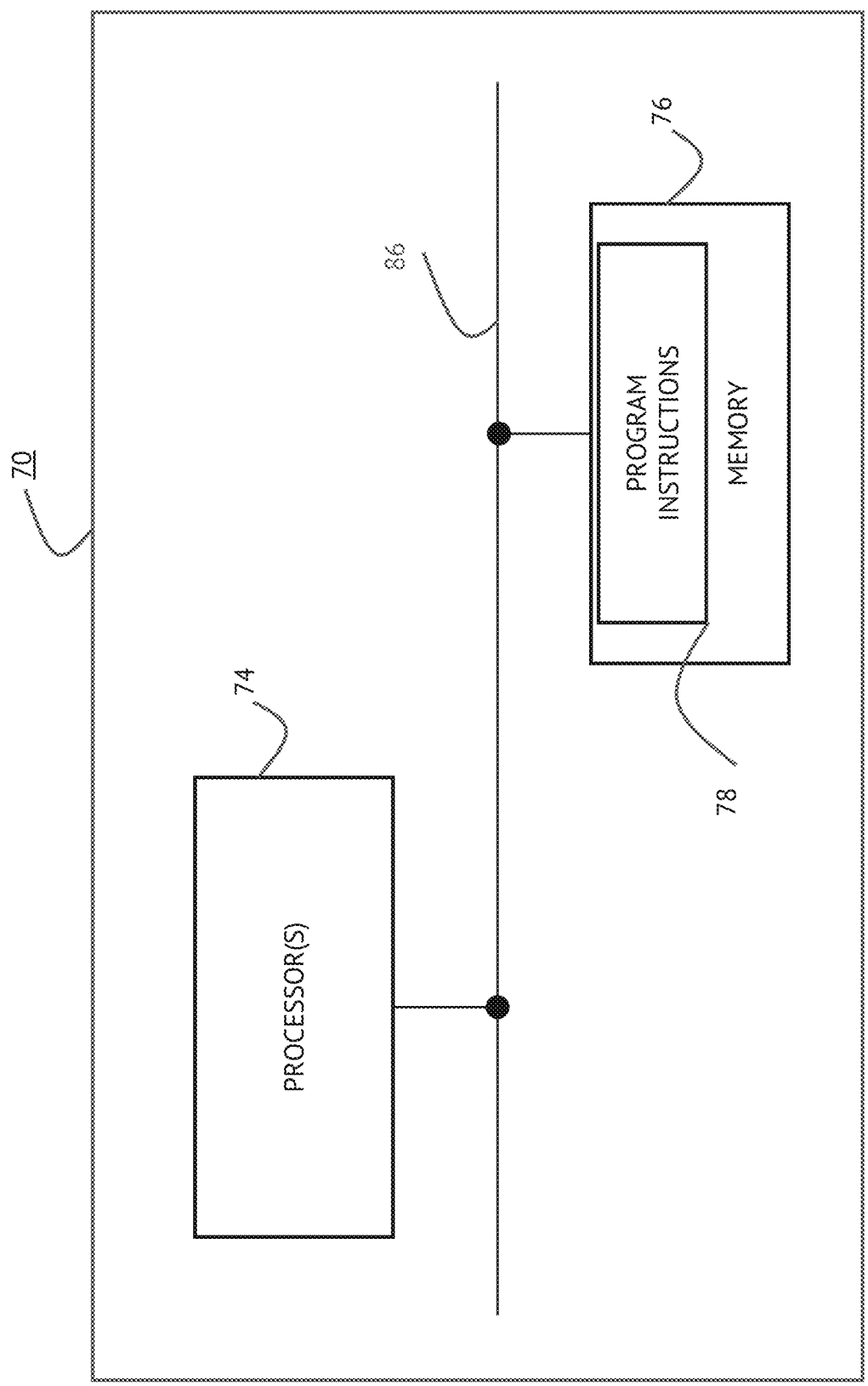

SYSTEMS AND METHODS OF MULTI-IMPLANT PATTERNED BRAIN IMAGING AND STIMULATION

CROSS REFERENCE TO RELATED APPLICATIONS

The present application claims priority to and the benefit of U.S. Provisional Application Ser. No. 62/588,088 entitled "Rotation Compensation for Brain Imaging and Stimulation," filed on 17 Nov. 2017, and U.S. U.S. Provisional Application Ser. No. 62/588,898 entitled "Multi-implant Patterned Stimulation," filed on 20 Nov. 2017, and a co-pending U.S. Nonprovisional application Ser. No. 16/177,372 entitled "Systems and Methods of Rotation Compensation for Brain Optical Imaging and Stimulation", filed on 31 Oct. 2018, the disclosures of which are incorporated herein by reference in their entireties.

BACKGROUND

Technical Field

The present disclosure relates to fields of neuroimaging (or brain imaging technologies) and stimulation, and more particularly to microendoscope with optical fiber for optical stimulation and fluorescence imaging.

Background Art

Neuroscience is a science discipline gaining an enormous amount of interests from researchers and scientists to enhance human understanding of physical, psychological and neurological conditions of brains for medical treatment and development of artificial intelligence. Microendoscope optical brain imaging provides a tool for the study and unraveling of mystery of neuroscience of animals. Optical fiber microendoscope is designed to stimulate neurons and image neural activity of animals as minimally invasive or non-invasive solutions.

One conventional solution provides a microendoscope to observe, research and study a free-moving animal with an imaging fiber typically fixed on the head of an animal. As the animal moves in a geographical area, the imaging fiber of the microendoscope gets twisted as the animal turns and rotates in different directions. The resulting torque from the twisting of the imaging fiber from the animal's head potentially could cause the imaging fiber to break. Even if the imaging fiber does not break, the resulting torque on the fixed imaging fiber on the animal's head may be too burdensome that the animal may be constrained from natural movements and instead turn back to comply with the forces as exerted from the torque on the animal, which in effect unnaturally affecting the animal's natural movements and behavior. Because each implant and imaging fiber can only cover a small region of the brain, multiple implants/fibers are required to study multiple regions of the brain and the interactions between the regions.

Accordingly, it is desirable to design a microendoscope with functional capabilities that would allow an animal to move freely while capturing optical images and stimulating neurons without impacting or constrain the natural motions of the animal. It is also desirable to be able to stimulate and image multiple brain regions.

SUMMARY OF THE INVENTION

Embodiments of the present disclosure are directed to instruments and methods that provide one or more stimulations with multiple fibers and multiple imaging implants inserted in a subject for stimulating neurons and capturing images from one or more regions of the subject's brain. A vast amount of combinations and/or permutations is possible with the multiple imaging implants to monitor and analyze different hemispheres of a brain, or multiple sites within the same hemisphere, as to observe how one or more stimulations projected on the certain sites on the brain's one hemisphere would cause responses to sites of the other hemisphere of the brain.

In a first embodiment, the microendoscope includes an optical instrument with a single spatial light modulator, a furcated imaging fiber bundle with multiple fibers, multi-implants coupled to a subject for multi-implant patterned brain imaging and stimulation. The single spatial light modulator is capable to project optical patterns to different imaging fibers by controlling the pixels of the spatial light modulator. The single spatial light modulator is able to stimulate different brain regions with different colors using two different methods. In one method, the single spatial light modulator adopts the field sequential color method to stimulate different imaging fibers with different colors. In another method, different regions of the spatial light modulator may be illuminated with different colors of light, thereby resulting different imaging fibers receiving different colors of stimulation optical patterns. A rotary joint is disposed between the spatial light modulator and the imaging implant to facilitate the movements and rotations of the imaging implant that is attached to the subject, thereby providing an essentially frictionless contact to brain of the subject so that the subject can freely move and rotate without feeling the cumbersome imaging implants and fibers that are attached to the subject.

In a second embodiment, the microendoscope comprises multiple spatial light modulators and multiple imaging implants for multi-implant patterned brain imaging and stimulation of the subject. Multiple spatial light modulators increase the flexibility and capabilities of the microendoscope. For example, each of the spatial light modulators can separately controlling a specific color on a particular imaging fiber, which provides true simultaneous multi-color stimulations, where the first spatial light modulator stimulates a blue color optical pattern onto to the first fiber and the first imaging implant, while the second spatial light modulator stimulates a red color optical pattern onto to the second fiber and the second imaging implant. Two spatial light modulators are illustrated in this embodiment, as one of skilled in the art would recognize that additional spatial light modulators can be added to the microendoscope by adding a different beamsplitter or a dichroic mirror for coupling the light into the objective lens for each additional spatial light modulator.

In a third embodiment, the microendoscope includes the single spatial light modulator, multiple imaging implants, and multiple cameras for multi-implant patterned brain imaging and stimulation of the subject. Multiple cameras enhance the overall functional capabilities of the microendoscope. For example, each camera can cover a selected imaging fiber or a selected number of imaging fibers, or a selected wavelength or color. One or more additional cameras can be added to the two cameras in the microendoscope with the addition of one or more beamsplitters or one or more dichroic mirrors.

Broadly stated, an apparatus, comprises an instrument including one or more cameras and one or more spatial light modulators; a plurality of imaging fibers, each imaging fiber having an instrument end coupled to the instrument and a distal end, the instrument ends in the plurality of imaging fibers being bundled together; and a plurality of imaging implants, each imaging implant coupled to a respective imaging fiber in the plurality of imaging fibers, the plurality of imaging implants inserted into multiple regions of a subject.

The structures and methods of the present disclosure are disclosed in detail in the description below. This summary does not purport to define the disclosure. The disclosure is defined by the claims. These and other embodiments, features, aspects, and advantages of the disclosure will become better understood with regard to the following description, appended claims, and accompanying drawings.

Additional features and advantages of embodiments will be set forth in the description, which follows, and in part will be apparent from the description. The objectives and other advantages of the invention will be realized and attained by the structure particularly pointed out in the example embodiments in the written description and claims hereof as well as the appended drawings. It is to be understood that both the foregoing general description and the following detailed description are illustrative and explanatory and are intended to provide further explanation of the invention as claimed.

BRIEF DESCRIPTION OF THE DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings wherein like reference numerals represent like elements and in which:

FIG. 8 is a simplified diagram of a computer processing system in accordance with the present invention.

DETAILED DESCRIPTION

Figure 1:
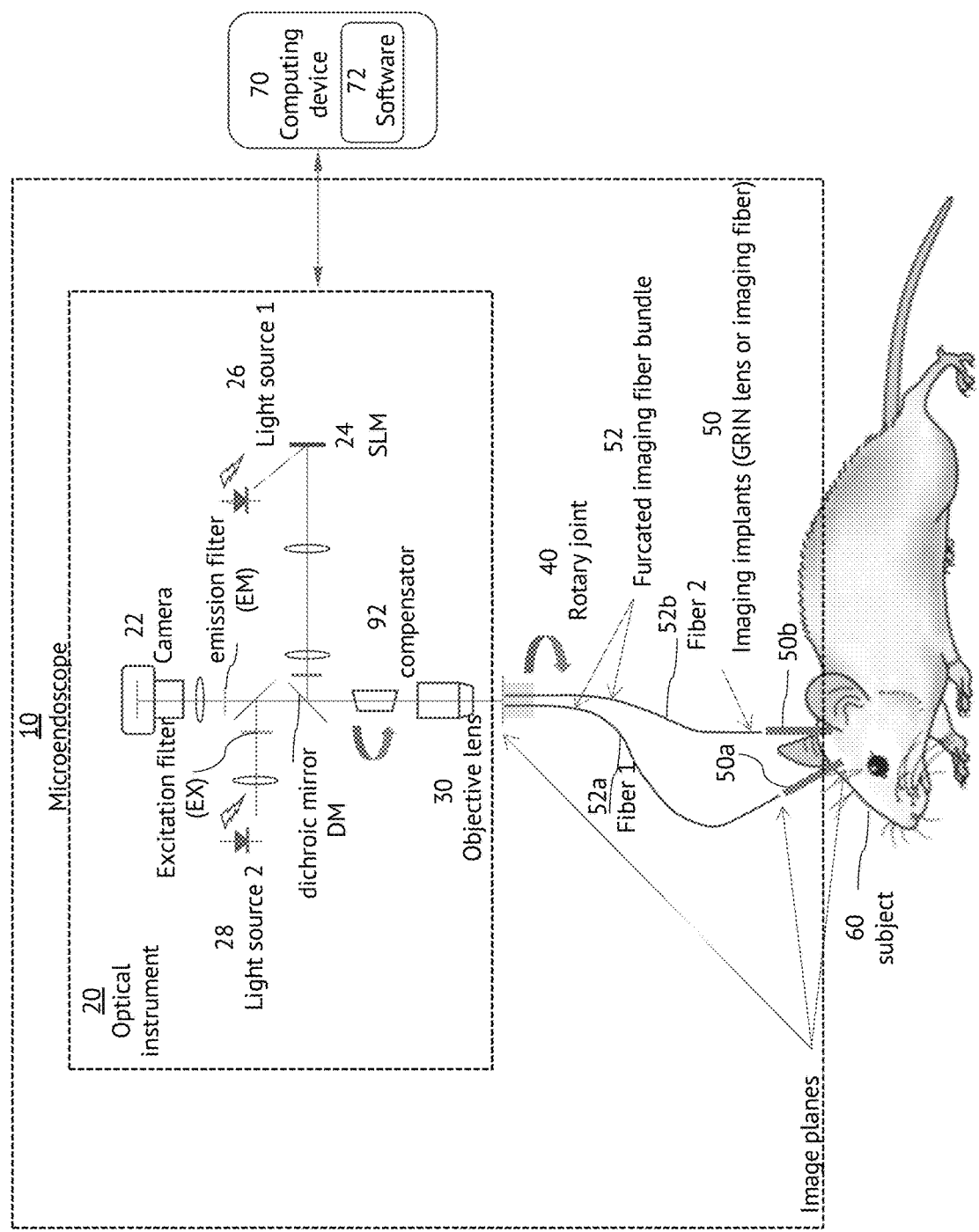
FIG. 1 is a system diagram illustrating a first embodiment of microendoscope with a single spatial light modulator and multiple implants for multi-implant patterned brain imaging and stimulation in accordance with the present invention.

A description of structural embodiments and methods of the present invention is provided with reference to FIGS. 1-5. It is to be understood that there is no intention to limit the invention to the specifically disclosed embodiments but that the invention may be operated using other features, elements, methods, and embodiments that are known to those of skill in the art. Like elements in various embodiments are commonly referred to with like reference numerals.

Different arrangements described herein are provided by way of example only, and other arrangements and elements can be added or used instead and some elements may be omitted altogether. Also, those skilled in the art will appreciate that many of the elements described herein are functional entities that may be implemented as discrete components or in conjunction with other components, in any suitable combination and location, and various functions could be carried out by software, firmware and/or hardware.

FIG. 1 is a system diagram illustrating a first embodiment of microendoscope 10 comprising an optical instrument 20 that includes a single spatial light modulator 24, a furcated imaging fiber bundle 52 with multiple fibers, and multi-implants (also referred to as "multiple implants) 50 coupled to a subject 60 for multi-implant patterned brain imaging and stimulation. The optical instrument 20 further includes a spatial light modulator (SLM) 24, a first light source 26, a second light source 28, a camera 22, a compensator 92, and an objective lens 30. The rotary joint 40 is disposed between the optical instrument 20 and the imaging implant 50. The rotary joint 40 allows the subject 60 to be able to move freely because the furcated imaging fiber bundle 52 and the imaging implant 50 rotate along the direction and movements of the subject 60. The rotary joint 40, for example, has ball bearings with low-friction, which enables the rotary joint 40 to rotate freely with the subject 60, without affecting the subject's 60 behavior or the rotational direction of the subject 60. The microendoscope 10 with multiple imaging implants 50a, 50b and multiple fibers 52a, 52b is suitable for conducting behavior studies to stimulate multiple areas of the subject's 60 brain, where each area selected cells are stimulated with optical patterns from the spatial light modulator 24.

A brain is generally divided into two hemispheres, the left hemisphere and the right hemisphere. The left hemisphere of a brain is understood to perform, logic (analytical, reasoning, mathematics, science, thinking in words, etc.). The right side of a brain is supposed to be more creative (arts, imagination, intuition, holistic thinking, etc.). The two hemispheres are interconnected and affect one other.

As an example, the spatial light modulator 24 is used to stimulate multiple regions of the subject's 60 brain with optical patterns through the furcated imaging fiber bundle 52. The spatial light modulator 24 projects an optical pattern onto the tip of the imaging fiber bundle 52. In one embodiment, the spatial light modulator 24 also has two circles, where a first circle could be used to send a light 26 to the fiber 52a, and a second circle could be used to send the light 26 to the fiber 52b. As an alternative embodiment, the spatial light modulator 24 can come from two light sources to sending to the two circles coupled to the fibers 52a, 52b, where the two light sources are optically matched to the fibers 52a, 52b. For example, the first light source 26 illuminates the spatial light modulator 24. A digital micromirror device (DMD), with an array of individually switchable mirrors, controls the pixels in which the spatial light modulator 24 sends a first light pattern to the first circle connected to the fiber 52a, which is connected to the left hemisphere of the subject 60, as well as the spatial light modulator 24 can control and send a second pattern to the second circle connected to the fiber 52b, which is then connected the right hemisphere of the subject 60. Hence, generating optical patterns through the imaging fibers 52a, 52b to different regions of the subject's 60 brain is dictated by controlling the spatial light modulator's 24 pixels in a region that is associated with a particular imaging fiber.

Multiple sites on the subject's brain can be stimulated and imaged with the microendoscope 10. The furcated imaging fiber bundle as illustrated in the first embodiment shows two fibers 52a, 52b, though the actual number of fibers can be selected depending on the objective in the optical imaging of the subject 60. Multiple implants 50 facilitate animal behavior studies where scientists and researchers seek to observe and analyze multiple regions of the subject's brain.

Various combinations of stimulation and imaging may be desirable by a scientist. One scenario is to provide stimulation to the left side of a brain, while observing the right side of the brain. Another scenario is the other way around, stimulating the right side of the brain and observing the left side of the brain. A scientist may also like to stimulate both the left hemisphere and the right hemisphere simultaneously, as well observing both hemispheres at the same time. As a further scenario, multiple sites on either the left hemisphere or the right hemisphere may be stimulated and observed. To image brain activities one can use light source 2(28) to excite fluorescence while use camera 22 to capture fluorescence images.

Figure 2:
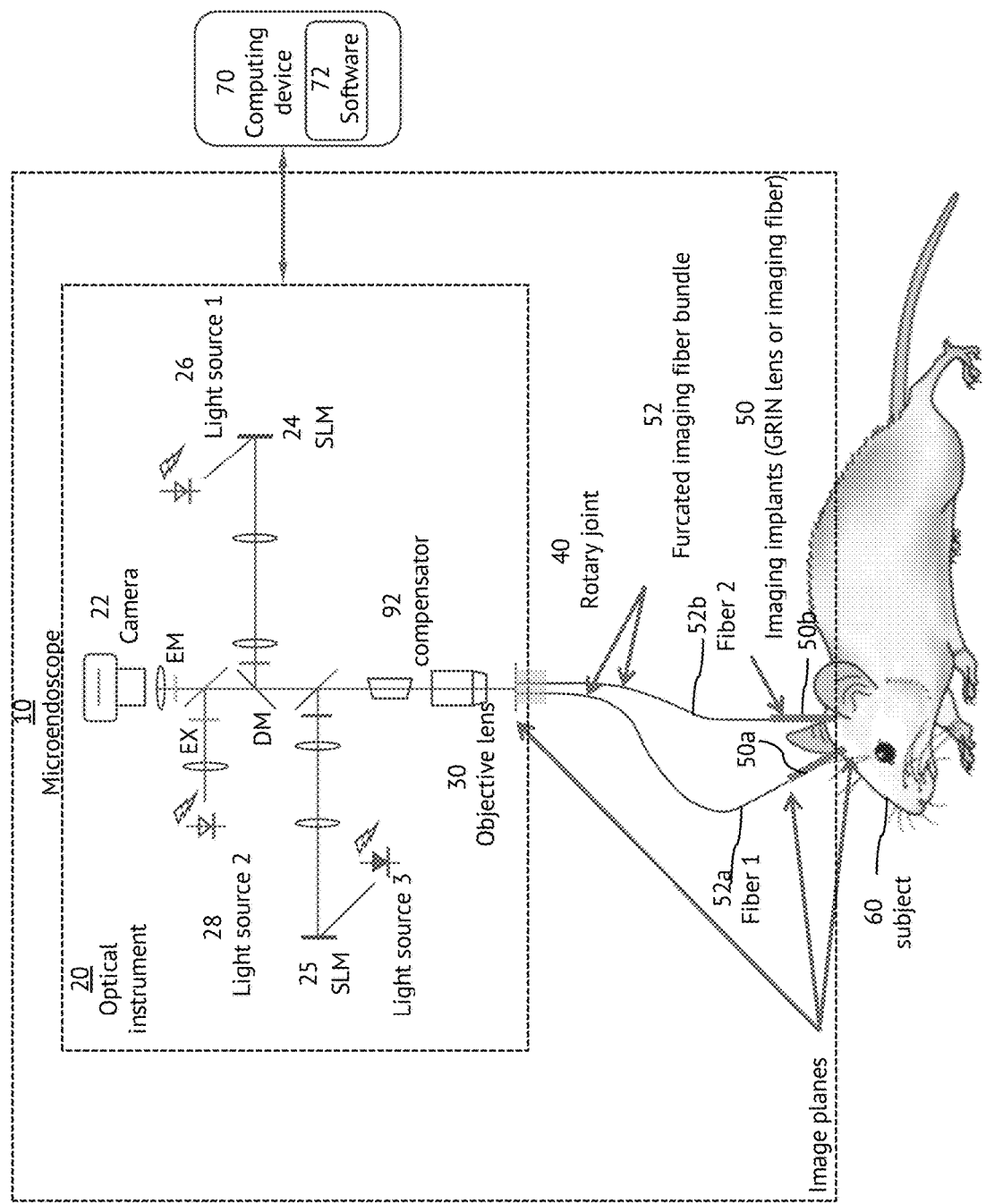
FIG. 2 is a system diagram illustrating a second embodiment of microendoscope with multiple spatial light modulators and multiple implants for multi-implant patterned brain imaging and stimulation in accordance with the present invention.

The capability to stimulate different brain regions with different colors can be accomplished with either a single spatial light modulator or multiple spatial light modulators (as illustrated in FIG. 2). Each spatial light modulator may cover a single imaging fiber or multiple imaging fibers. With the microendoscope 10 implemented with a single spatial light modulator, different imaging fibers may receive different colors through the field sequential color method. For additional information on methods for generating interleaved multi-wavelength images with a single spatial light modulator, see U.S. Pat. No. 10,039,934 entitled "Multi-Wavelength Interleaved Optical Stimulation" by Song Peng, the disclosure of which is incorporated herein by reference in its entirety. Alternatively, different regions of the spatial light modulator 24 may be illuminated with different colors (or wavelengths) of light, resulting in different imaging fibers receiving different colors of stimulation.

Multiple imaging implants 50 are inserted into the brain of the subject 60 for stimulation and imaging. In this embodiment, two imaging implants, 50a, 50b, are illustrated in FIG. 1. Many more imaging implants can be added to the multiple imaging implants 50 for insertion into the subject to provide a greater coverage in the total number of stimulation and imaging.

Each of the imaging implants 50a, 50b is associated with a respective implant fiber 52a, 52b to provide a communication medium from the spatial light modulator 24 to provide stimulation to the subject 60, or take back the captured images back to the optical instrument 20 in the microendoscope 10. In one embodiment, each of the multiple imaging fibers 50a, 50b is separately inserted into the brain of the subject 60, and the fibers 52a, 52b are combined into a furcated imaging fiber bundle 52 for sending the captured images back to the optical instrument 20 in the microendoscope 10. The two fibers 52a, 52b are then coupled to the camera 22 in which the camera 22 observes two circles where a first circle represents the connection to the fiber 52a and a second circle represents the connection to the fiber 52b.

The camera 22 detects, monitors and analyzes certain fixed feature of the images or specimen from the subject generated from the tip of the imaging fibers 50a, 50b. The camera 22 monitors the stimulation sites and for observing the activities of the brain regions of the subject 60. In the first embodiment, one single camera 22 is used to cover the imaging fibers 52a, 52b. Images inside the camera 22 are also rotating as the rotary joint 40 and the imaging implants 50a, 50b move with the subject 60.

Each of the imaging implants 50a, 50b can be implemented, for example, with a gradient index (GRIN) lens or a short piece of imaging fiber. Alternatively, the rotary joint 40 can also be placed between a gradient index (GRIN) lens implant and the imaging fiber. The subject in instance is an animal, such as a mouse.

The rotation compensator 92 serves to rotate back an optical image received from the imaging implant 50 of the subject 60. One suitable implementation of the rotation compensator 92 is a Dove prism. The correlation between an optical image and the Dove prism is that the output image rotates at twice the rotation speed of the Dove prism. One way to achieve this rotation ratio employs mechanical mechanisms to link the rotary joint 40 and the rotation compensator 92 which yield the rotation compensator 92 rotates at the half the speed relative to the rotational speed of the rotary joint 40. Preferably, in the example of implementing with a Dove prism, the rotation compensator 92 would rotate in the same direction as the direction of the rotary joint 40. The output image from the rotation compensator 92 remains stationary even as the subject 60 moves around. The stimulation patter from the spatial light modulator 24 also stays stationary on the specimen.

Optionally, an electrical motor can be added to enhance power assistance to the rotation compensator 92, particularly in embodiments where a chosen prism may be on the heavy side, as to hinder the movements of the subject or the weight of the rotation compensator 92 potentially could cause the fiber 52 to break. The addition of the electrical motor would assist the fiber to withstand the weight of the prism without breaking the fiber.

A computing device 70 is optionally coupled to the optical instrument 20 to extract rotation angles from the position of fixed feature or an image of the specimen of the subject 60 from the camera 22. The computing device 70 includes an imaging software 72 for adjusting and realigning each affected image based with the rotation angles. With the computation on the rotation angles, the spatial light modulator 24 in the microendoscope 10 is able to rotate the stimulation patterns by the specified rotation angles to offset the rotational directions and movements of the subject 60. The microendoscope 10 in the first embodiment comprises a system solution without the need of a rotation compensator by a combination of the rotary joint 40 that follows the natural movements of the imaging implant 50 attached to the subject 60, which then the camera 10 receives rotated images from the tip of the imaging implant 50 that the imaging software 72 calculates the amount of rotated angles, followed by the spatial light modulator 24 correspondingly adjusting the projected stimulation pattern by the specified rotated angled on to the brain of the subject 60.

FIG. 2 is a system diagram illustrating a second embodiment of microendoscope 10 with multiple spatial light modulators 24, 25 and multiple imaging implants 50a, 50b for multi-implant patterned brain imaging and stimulation of the subject 60. Multiple spatial light modulators 24, 25 increase the flexibility and capabilities of the microendoscope 10. In one operational mode, each of the spatial light modulators 24, 25 can separately controlling a specific color on a particular imaging fiber, which provides true simultaneous multi-color stimulations. For example, the first spatial light modulator 24 stimulates a blue color optical pattern onto to the first fiber 52a and the first imaging implant 50a, while the second spatial light modulator 25 stimulates a red color optical pattern onto to the second fiber 52b and the second imaging implant 50b. Additional spatial light modulators can be added to the two spatial light modulators 24, 25 in FIG. 2, which requires a different beamsplitter or a dichroic mirror for coupling the light into the objective lens for each additional spatial light modulator.

Although as described above in the first embodiment that a single spatial light modulator is able to interleave two colors with fast pulses, as further elaborated in U.S. Pat. No. 10,039,934, the stimulation of two colors may be more simpler achieved with two spatial light modulators 24, 25.

Figure 3:
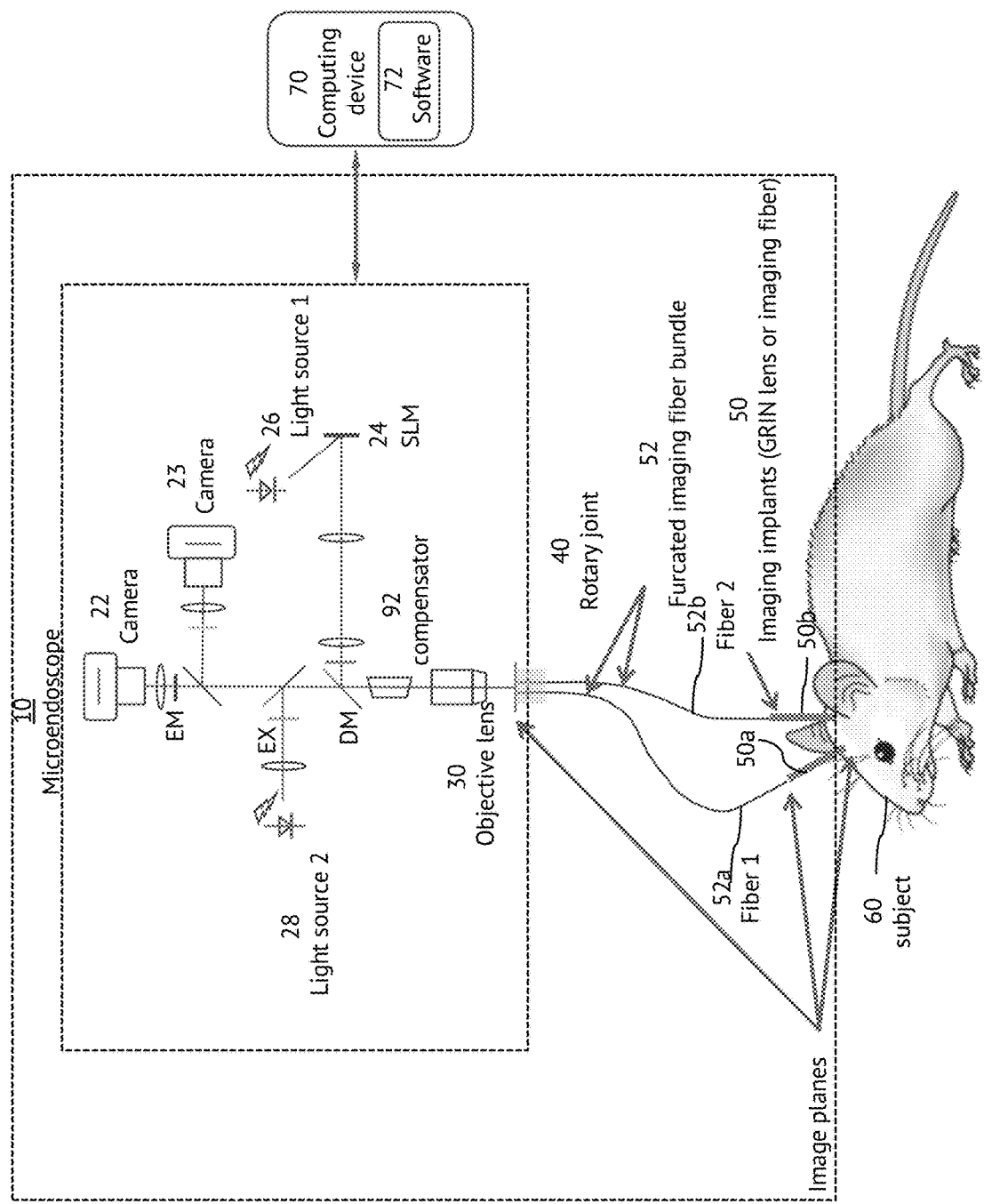
FIG. 3 is a system diagram illustrating a third embodiment of microendoscope with a single spatial light modulator, multiple implants and multiple cameras for multi-implant patterned brain imaging and stimulation in accordance with the present invention.

FIG. 3 is a system diagram illustrating a third embodiment of microendoscope 10 with the single spatial light modulator 24, multiple imaging implants 50a, 50b and multiple cameras 22, 23 for multi-implant patterned brain imaging and stimulation of the subject 60. Multiple cameras 22, 23 provide greater functional capabilities, such as each camera covers a selected imaging fiber or a selected number of imaging fibers, or a selected wavelength (or color). One or more additional cameras can be added to cameras 22, 23 as part of the optical instrument 20 in the microendoscope 10 with the addition of one or more beamsplitters or one or more dichroic mirrors. Fluorescence imaging excitation and emission filters can also be used in the optical instrument 20.

In one embodiment, the optical instrument 20 in the microendoscope 10 is designed which provides the capability to easily switching the beamsplitter, dichroics, or filters in order to facilitate the different optical pattern simulation or different imaging color. As an example, interchangeable beamsplitter, dichroics, or filters may be placed on a mechanical rail or similar devices for users to easily deploy a different combination or combinations of beamsplitter, dichroics, or filters.

Figure 4:
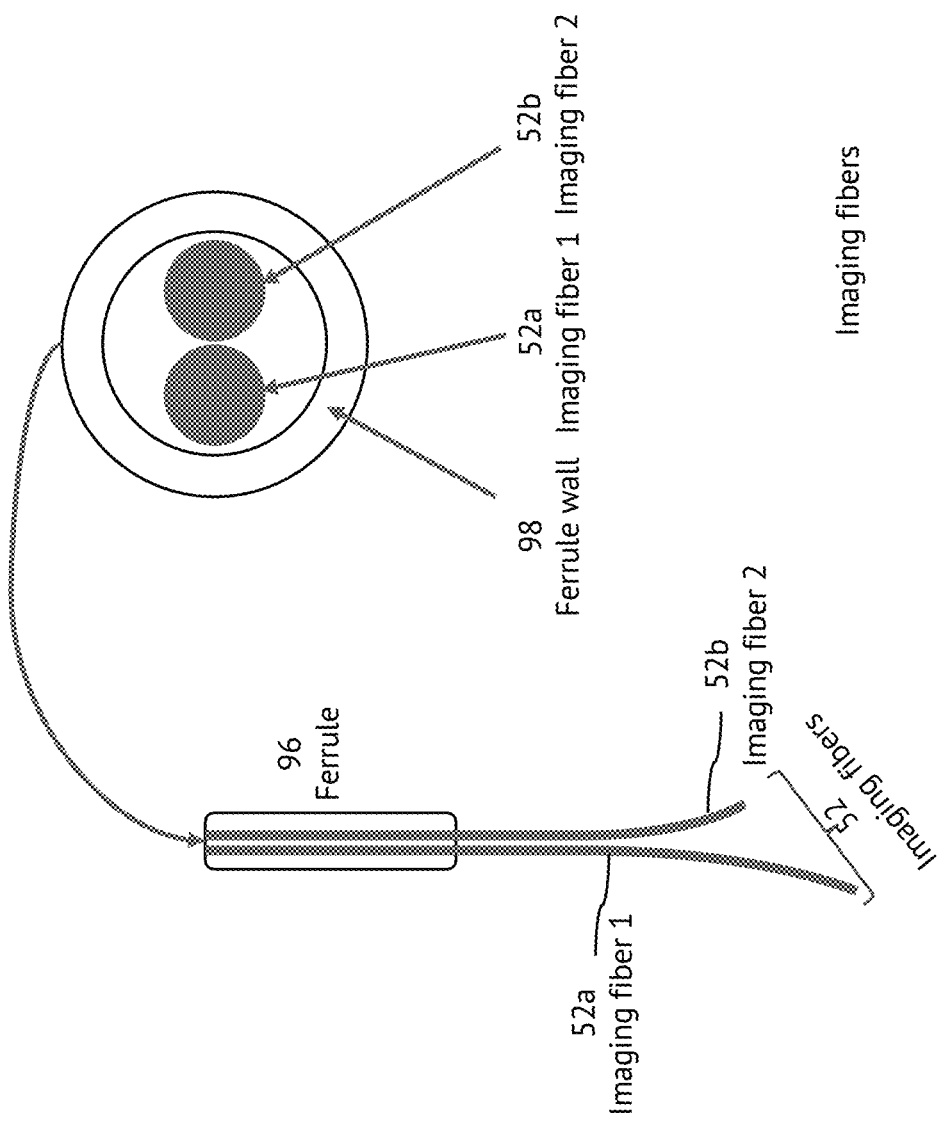
FIG. 4 is a system diagram illustrating an example of furcated imaging fibers with a ferrule in accordance with the present invention.

FIG. 4 is a system diagram illustrating an example of furcated imaging fibers 52 with a ferrule 96. With the furcated imaging fiber bundle 52 that contains multiple imaging fibers 52a, 52b, the common ends of the bundle 52 would be coupled to the rotary joint 40, while the distal ends of the imaging fibers 52a, 52b are used to image and stimulate different regions of the subject 60. In this embodiment with two fibers, these are two separate fibers on the end closer to the subject 60, the first imaging fiber 52a coupled to one region of the subject 60 and the second imaging fiber 52b coupled to the same or different region of the subject 60. On the other end of this embodiment, the ferrule 96 includes a ferrule wall 98 that houses the two imaging fibers 52a, 52b, within the ferrule wall 98. The imaging fibers 52a and 52b appear as two circles on the other end that are coupled to the spatial light modulator 24 or the camera 22. The ferrule 96 can be implemented as a solid metal tube which the two imaging fibers 52a, 52b that are placed side by side within the ferrule wall 98.

The above embodiments illustrate microendscope concepts with the furcated imaging fiber bundle 52. However, one of skilled in the art would know that it would also be possible to perform multi-color stimulation and imaging through any one of the imaging fibers 52a or 52b in the furcated imaging fiber bundle 52 by using multiband dichroic and filters In some embodiments, the microendoscope 10 can also be used to stimulate through a first group of one or more imaging fibers, while observing through a second group of one or more imaging fibers. The one or more imaging fibers in the first group and the second group may or may not overlap with one another.

In some embodiments, the microendoscope 10 in FIGS. 1-3 can be used for researching and experimentation on multiple subjects or animals. The imaging implants and corresponding imaging fibers are installed selectively on different animals.

Optionally, an angle encoder can be added to operate with the rotary joint 40 to be able to directly feed a rotation angle to a motor to rotate the rotation compensator, thereby eliminates any mechanical connection between the rotary joint and the rotation compensator. Alternatively, without a rotation encoder, other embodiments described above to obtain a rotated angle from an optical image can be used to control the rotation compensator for compensating the orientation of the rotated optical image. For additional information on the angle encoder, see U.S. application Ser. No. 16/177,372, "Systems and Methods of Rotation Compensation for Brain Optical Imaging and Stimulation" by Song Peng, the disclosure of which is incorporated herein by reference in its entirety.

Figure 5:
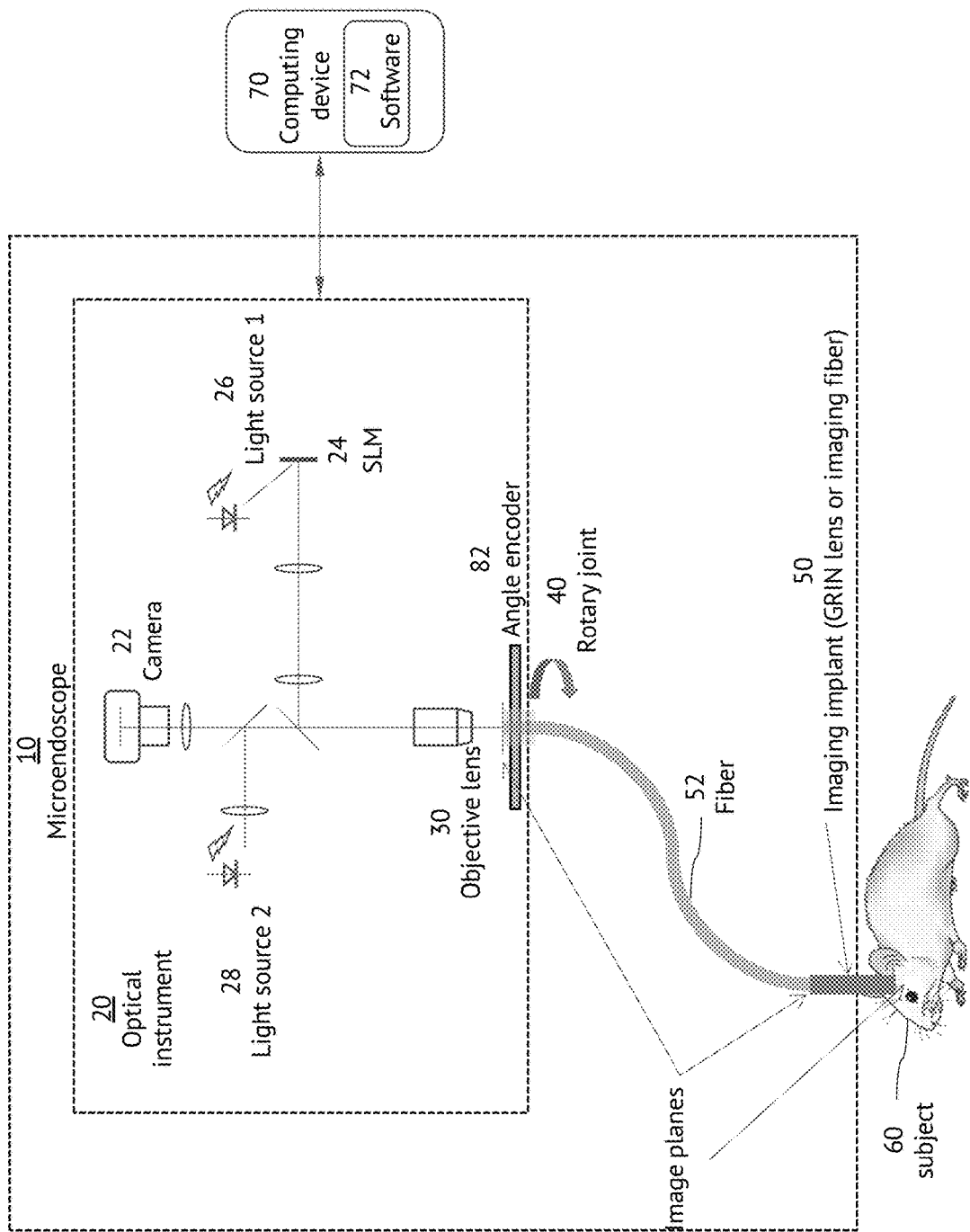
FIG. 5 is a system diagram illustrating a second embodiment of microendoscope with a rotary joint and an angle encoder in accordance with the present invention.

FIG. 5 is a system diagram illustrating a second embodiment of microendoscope 10 with a rotary joint 40 and an angle encoder 82 (also referred to as a rotation encoder). The microendoscope 10 includes the angle encoder 82, which is coupled to the rotary joint 40, for a more accurate read out of the rotation angles with a shorter delay. The angle encoder 82 produces angular information of the images captured by the imaging plant 50 to the computing device 70 for realigning the images, as well as for the spatial light modulator 24 to rotate the stimulation patterns.

Figure 6:
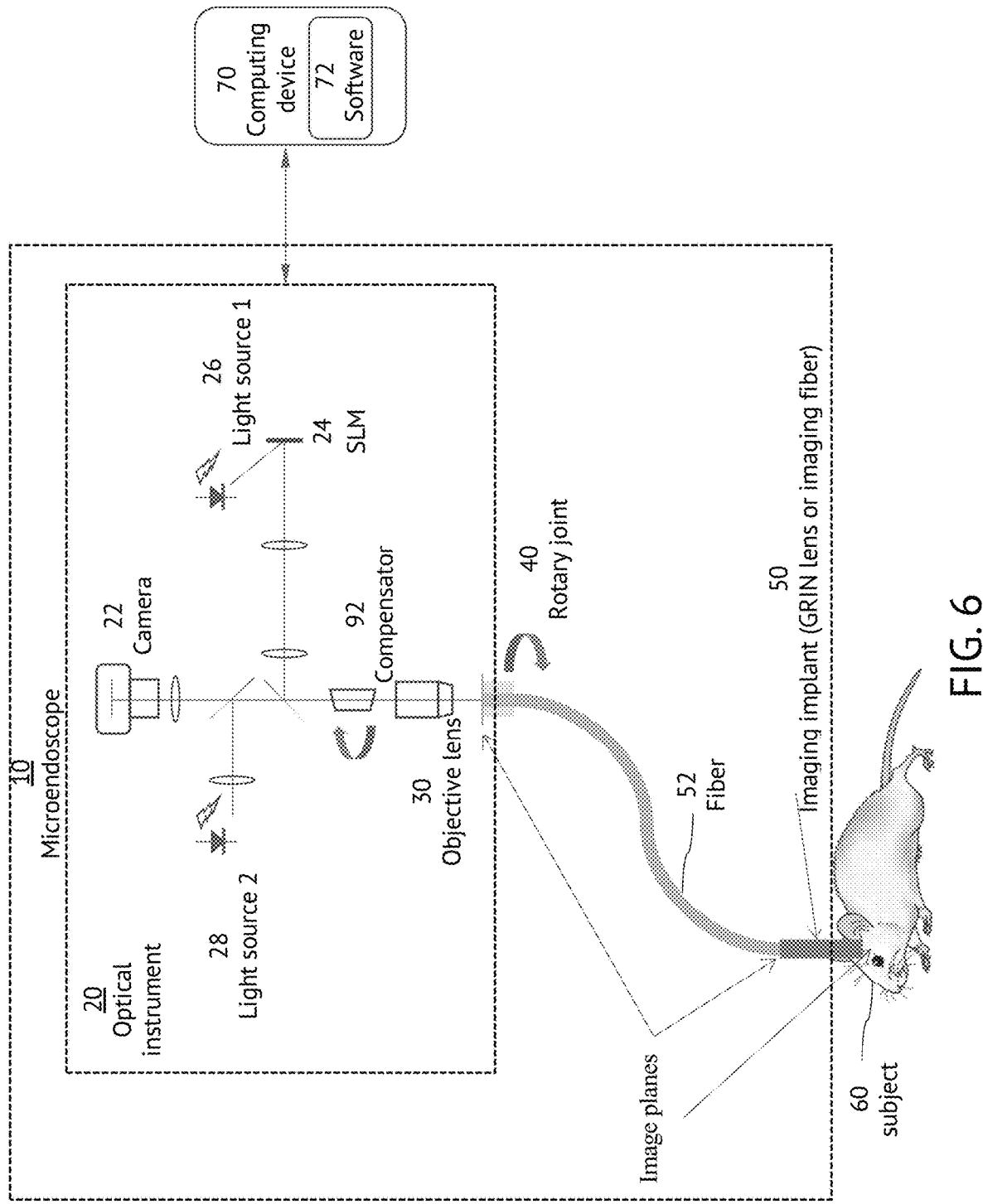
FIG. 6 is a system diagram illustrating a third embodiment of microendoscope with a rotary joint and a rotation compensator in accordance with the present invention.

FIG. 6 is a system diagram illustrating a third embodiment of the microendoscope 10 with the rotary joint 40 and a rotation compensator 92. The rotation compensator 92 serves to rotate back an optical image received from the imaging implant 50 of the subject 60. One suitable implementation of the rotation compensator 92 is a Dove prism. The correlation between an optical image and the Dove prism is that the output image rotates at twice the rotation speed of the Dove prism. One way to achieve this rotation ratio employs mechanical mechanisms to link the rotary joint 40 and the rotation compensator 92 which yield the rotation compensator 92 rotates at the half the speed relative to the rotational speed of the rotary joint 40. Preferably, in the example of implementing with a Dove prism, the rotation compensator 92 would rotate in the same direction as the direction of the rotary joint 40. The output image from the rotation compensator 92 remains stationary even as the subject 60 moves around. The stimulation patter from the spatial light modulator 24 also stays stationary on the specimen.

Figure 7:
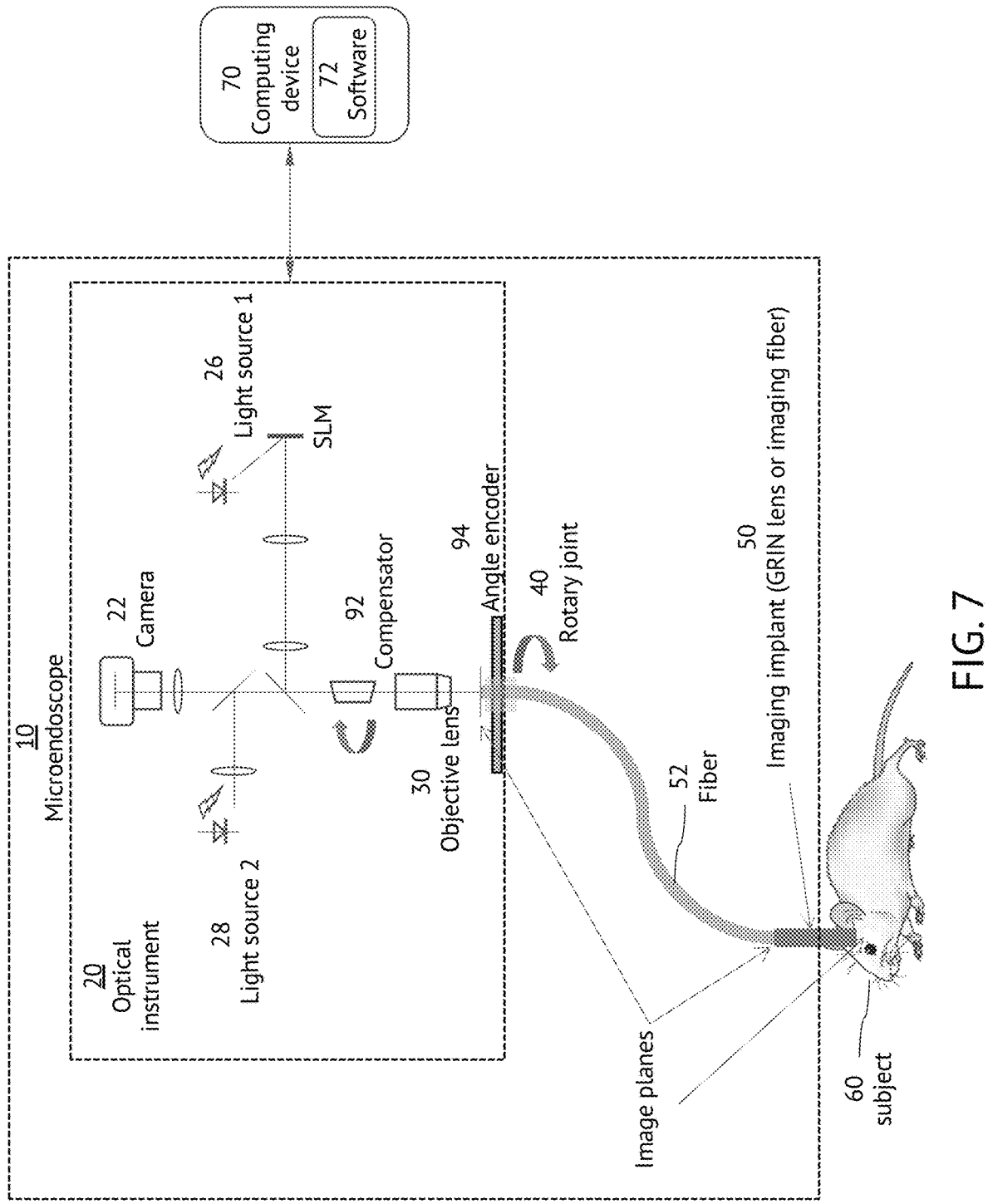
FIG. 7 is a system diagram illustrating a fourth embodiment of microendoscope with a rotary joint, a rotation compensator and an angle encoder in accordance with the present invention.

FIG. 7 is a system diagram illustrating a fourth embodiment of the microendoscope 10 with the rotary joint 40, the rotation compensator 92 and an angle encoder 94. The combination of the encoder 94 and the rotary joint 40 is able to directly feed a rotation angle to a motor to rotate the rotation compensator, thereby eliminates any mechanical connection between the rotary joint and the rotation compensator. Alternatively, without a rotation encoder, other embodiments described above to obtain a rotated angle from an optical image can be used to control the rotation compensator for compensating the orientation of the rotated optical image.

Various functions described herein, such as in FIG. 1-3 above, could be carried out by a processing system 70, as shown in FIG. 5. The system 70 includes at least one processor 74 and memory 76, coupled together via a bus 86. The processing system 70 may be, for example, incorporated in a separate controller controlling the element(s) of the microendoscope 10 (e.g., the spatial light modulato 24) or its components may be distributed fully or partially across the element(s) of the microendoscope 10. Various examples are possible.

In one embodiment, the processor(s) 74 may be dedicated processor(s) or general purpose processor(s) configured to execute computer-readable program code. The memory 76 may be volatile or non-volatile non-transitory computer-readable medium or media, now known or later developed. The memory 76 may hold program logic comprising program instructions 78 (e.g., machine language instructions) executable by the processor(s) 74 to carry out various functions described herein. Additionally, the memory 76 may store any other data, such as data used by the processor(s) 74 in the execution of the program instructions 78. However, any additional data may also be held in other data storage location(s) separate from the memory 76.

Further, although not shown in FIG. 7, the processing system 70 may include a number of interfaces, such as user interface(s), communication interface(s) (e.g., an interface for communicating data to/from the memory 76, etc.), and/or the like. Also, other elements (e.g., modules, input lines, buses, etc.) may be included as well.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B are satisfied by any one of the following: A is true (or present) and B is fake (or not present), A is fake (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention can be implemented in numerous ways, including as a process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to some possible embodiments. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component. An ordinary artisan should require no additional explanation in developing the methods and systems described herein but may nevertheless find some possibly helpful guidance in the preparation of these methods and systems by examining standard reference works in the relevant art.

These and other changes can be made to the invention in light of the above detailed description. In general, in the following claims, the terms used should not be construed to limit the invention to the specific embodiments disclosed in the specification and the claims, but should be construed to include all methods and systems that operate under the claims set forth herein below. Accordingly, the invention is not limited by the invention, but instead its scope is to be determined entirely by the following claims.

What is claimed and desired to be secured by Letters Patent of the United States is:

1. An apparatus, comprising:
    an instrument including one or more cameras and the one or more spatial light modulators (SLMs);
    a plurality of imaging fiber bundles, each imaging fiber bundle having a plurality of cores, each imaging fiber bundle transmitting a two-dimensional image, each imaging fiber bundle having an instrument end coupled to the instrument at distal end of the fiber bundle, the instrument ends in the plurality of imaging fiber bundles being bundled together;
    a plurality of imaging implants, each imaging implant coupled to a respective imaging fiber bundle in the plurality of imaging fiber bundles, the plurality of imaging implants inserted into multiple regions of a subject; and
    a rotatory joint coupled to the plurality of imaging fiber bundles and the instrument between the instrument and the plurality of imaging fiber bundles, the rotary joint rotating along with motion of the subject through the imaging implant and imaging fiber bundles,
    wherein the imaging fiber bundles pass through the rotatory joint and are aligned with and connected to the one or more cameras and the one or more SLMs even when the imaging fiber is being rotated.

2. The apparatus of claim 1, wherein the one or more spatial light modulators comprises one spatial light modulator having an active area assigned into a plurality of regions, each region of the active area in the spatial light modulator controlling an imaging fiber bundle in the plurality of imaging fiber bundles.

3. The apparatus of claim 1, wherein the one or more spatial light modulators comprises a plurality of spatial light modulators, each spatial light modulator controlling a subset of imaging fiber bundles that is non-mutually exclusive with respect to another spatial light modulator controlling another subset of imaging fiber bundles.

4. The apparatus of claim 1, wherein the one or more cameras comprises one camera having an active area assigned into a plurality of regions, each region of the active area in the camera capturing an imaging fiber bundles in the plurality of imaging fiber bundles.

5. The apparatus of claim 1, wherein the one or more cameras comprises a plurality of cameras, each camera capturing a subset of imaging fiber bundles that is non-mutually exclusive with respect to another camera capturing another subset of imaging fiber bundles.

6. The apparatus of claim 1, wherein one or more spatial light modulators is used for controlling a first subset in the plurality of imaging fiber bundles, and wherein one or more cameras is used for capturing a second subset in the plurality of imaging fiber bundles, the first subset in the plurality of imaging fiber bundles being non-mutually exclusive of the second subset in the plurality of imaging fiber bundles.

7. The apparatus of claim 1, wherein the instrument comprises one or more imaging optics for imaging the instrument ends of the imaging fiber bundles onto the one or more cameras.

8. The apparatus of claim 1, wherein the instrument comprises one or more projection optics for projecting the one or more spatial light modulators onto the instrument ends of the imaging fiber bundles.

9. The apparatus of claim 1, wherein the instrument comprises one or more light sources for illuminating the subject.

10. The apparatus of claim 1, wherein the instrument comprises one or more light sources for stimulating the subject.

11. The apparatus of claim 1, wherein the plurality of imaging implant comprises a plurality of gradient index (GRIN) lens.

12. The apparatus of claim 1, wherein the plurality of imaging implants comprise a plurality of imaging fiber bundles.

13. The apparatus of claim 1, wherein the instrument comprises an angle encoder, coupled to the rotary joint, for reading out the rotating angle of the instrument end of the imaging fiber bundle as the subject moves.

14. The apparatus of claim 1, wherein the instrument comprises a rotation compensator disposed in an optical path for compensating the image rotation caused by the movement of the subject.

15. The apparatus of claim 1, wherein the rotation compensator comprises a Dove prism, the Dove prism rotating at half of the speed of the rotary joint.

16. The apparatus of claim 1, wherein the instrument comprises:
   an angle encoder, coupled to the rotary joint, for reading out the rotating angle of the instrument end of the imaging fiber bundle as the subject moves;
   a rotation compensator disposed in an optical path for compensating the image rotation caused by the movement of the subject, the rotation compensator driven by a motor; and
   a controller for reading the angle information from the angle encoder and controlling the rotation compensation based on the received angle information.

17. The apparatus of claim 1, wherein the rotation compensator comprises a Dove prism, the Dove prism rotating at a fraction of the speed of the rotary joint.

18. The apparatus of claim 1, wherein the apparatus comprises a microendoscope.

* * * * *